United States Patent
Tatarkiewicz (10) Patent No.: US 10,514,331 B1
(45) Date of Patent: Dec. 24, 2019

(54) METHOD FOR DETERMINING THE SIZE OF NANOPARTICLES IN A COLLOID

(71) Applicant: HORIBA Instruments, Inc., Irvine, CA (US)

(72) Inventor: Jan J. Tatarkiewicz, San Diego, CA (US)

(73) Assignee: HORIBA Instruments Incorporated, Irvine, CA (US)

( * ) Notice: Subject to any disclaimer, the term of this patent is extended or adjusted under 35 U.S.C. 154(b) by 0 days.

(21) Appl. No.: 16/391,870

(22) Filed: Apr. 23, 2019

Related U.S. Application Data (63) Continuation of application No. 16/362,636, filed on Mar. 23, 2019, now abandoned.

(51) Int. Cl.
*G01N 15/02* (2006.01)
*G01N 15/00* (2006.01)

(52) U.S. Cl.
CPC ..... *G01N 15/0211* (2013.01); *G01N 15/0227* (2013.01); *G01N 2015/0038* (2013.01); *G01N 2015/03* (2013.01)

(58) Field of Classification Search
CPC ........... G01N 15/0211; G01N 15/0227; G01N 2015/0038; G01N 2015/03
USPC ................................................. 356/335–343
See application file for complete search history.

(56) References Cited

U.S. PATENT DOCUMENTS

2014/0152978 A1* 6/2014 Carr .................... G01N 15/0211
356/73

* cited by examiner

*Primary Examiner* — Tri T Ton
(74) *Attorney, Agent, or Firm* — Manuel de la Cerra (57) ABSTRACT

The system includes an adjustable light source constructed to direct a beam of electromagnetic radiation at a specimen chamber that allows a portion of the beam to scatter when illuminating particles within the chamber. The scattered portion of the beam is directed to a sensor, the sensor having a frame rate and a time period between frames. The system may have a processor connected to the sensor and light source, the processor may perform the following steps: activate the light source and obtain images from sensor; if the images from the sensor show that particles are blinking then reduce the frame rate, set the exposure time to at least 60% of the time between frames and reduce the illumination. Then, the processor obtains additional images and processes those images to mitigate blurring. The processor determines the Brownian motion of the particles from the processed images and determines the sizes of the particles based on the motion.

12 Claims, 6 Drawing Sheets

FIG. 4A
METHOD 100

METHOD FOR DETERMINING THE SIZE OF NANOPARTICLES IN A COLLOID

1.0 TECHNICAL FIELD

The present invention relates to measurement and observation of nanoparticles in liquid samples using a microscope equipped with a digital video camera.

2.0 RELATED APPLICATIONS

This application is also related to U.S. Provisional Patent Application No. 62/357,777 filed on Jul. 1, 2016, titled "METHOD FOR CALIBRATING INVESTIGATED VOLUME FOR LIGHT SHEET BASED NANOPARTICLE TRACKING AND COUNTING APPARATUS"; to U.S. Provisional Patent Application No. 62/372,025 filed on Aug. 8, 2016, titled "METHOD FOR CALIBRATING INVESTIGATED VOLUME FOR LIGHT SHEET BASED NANOPARTICLE TRACKING AND COUNTING APPARATUS"; to U.S. Provisional Patent Application No. 62/421,585 filed on Nov. 14, 2016, titled "METHOD FOR CALIBRATING INVESTIGATED VOLUME FOR LIGHT SHEET BASED NANOPARTICLE TRACKING AND COUNTING APPARATUS"; to U.S. Provisional Patent Application No. 62/241,354 filed on Oct. 14, 2015, titled "APPARATUS FOR MEASUREMENTS OF GROWTH OR DISSOLUTION KINETICS OF COLLOIDAL NANOPARTICLE"; to U.S. patent application Ser. No. 15/293,180, filed on Oct. 16, 2016, titled "APPARATUS AND METHOD FOR MEASUREMENT OF GROWTH OR DISSOLUTION KINETICS OF COLLOIDAL PARTICLES"; to U.S. patent application Ser. No. 15/018,532 filed on Feb. 8, 2016, titled "MULTI-CAMERA APPARATUS FOR OBSERVATION OF MICROSCOPIC MOVEMENTS AND COUNTING OF PARTICLES IN COLLOIDS AND ITS CALIBRATION"; to U.S. patent application Ser. No. 15/194,823, filed on Jun. 28, 2016, titled "SPECIAL PURPOSE CUVETTE ASSEMBLY AND METHOD FOR OPTICAL MICROSCOPY OF NANOPARTICLES IN LIQUIDS" issued on Jan. 10, 2017 as U.S. Pat. No. 9,541,490; to U.S. patent application Ser. No. 14/730,138, filed on Jun. 3, 2015, titled "NANOPARTICLE ANALYZER", issued on May 9, 2017 as U.S. Pat. No. 9,645,070; to U.S. patent application Ser. No. 15/399,679, filed on Jan. 5, 2017, titled "SPECIAL PURPOSE CUVETTE ASSEMBLY AND METHOD FOR OPTICAL MICROSCOPY OF NANOPARTICLES IN LIQUIDS"; to U.S. patent application Ser. No. 15/594,967, filed on May 15, 2017, titled "SPECIAL PURPOSE CUVETTE ASSEMBLY AND METHOD FOR OPTICAL MICROSCOPY OF NANOPARTICLES IN LIQUIDS"; and to U.S. Patent Application No. 62/187,391 filed on Jul. 1, 2015, titled "SPECIAL PURPOSE CUVETTE ASSEMBLY AND METHOD FOR OPTICAL MICROSCOPY OF NANOPARTICLES IN LIQUIDS"; the disclosures of all of the above patents are herein incorporated by reference in their entirety.

3.0 BACKGROUND

Nanoparticles are ubiquitous and by far the most abundant particle-like entities in natural environments on Earth and are widespread across many applications associated with human activities. There are many types of naturally occurring nanoparticles and man-made (engineered) nanoparticles. Nanoparticles occur in air, aquatic environments, rain water, drinking water, biofluids, pharmaceuticals, drug delivery and therapeutic products, and in a broad range of many industrial products. Nanoparticles usually occur within polydisperse assemblages, which are characterized by co-occurrence of differently-sized particles.

Nanoparticles are (as per ISO definition) particles smaller than 100 nm in diameter (more precisely, each of three Cartesian dimensions is smaller than 100 nm). However, in practical applications, this range has been extended into sub-micron or smaller than 1000 nm diameters. The latter is sometimes called mesoscale.

Given the widespread usage of nanoparticles, the ability to control and accurately characterize their properties may be useful to many applications. Conventional methods for measuring nanoparticle properties include Nanoparticle Tracking Analysis, which uses a microscope and video camera to analyze frames of the recorded videos to track images of light reflected or scattered by the nanoparticles undergoing Brownian motion.

Analysis of Brownian motion of nanoparticles allows for their sizing as described by A. Einstein (1905 Annalen der Physik 17 pp. 549-560) and is based on the simple assumption that such particles are more or less spherical, which means that their random movements are equally probable in all directions. Currently laser light sources with suitable optics are used, which allow for the creation of a very narrow light sheet, and the light scattering off the nanoparticles is observed at a right angle. This is called dark field microscopy. This type of microscopy, however, assumes that the nanoparticles can continuously scatter light, thus creating images with stable intensity (not changing much in time) to allow for uninterrupted tracking of particles' movements by the software. Both above mentioned assumptions (spherical and continuous light scattering) are frequently not possible. The most obvious example is that highly elongated particles like tobacco mosaic viruses (TMVs) look like rods with a diameter of about 20 nm and a length of about 300 nm, having a surface resembling a corn cob, as witnessed by TEM images, cf. e.g. P. Ge and Z. H. Zhou 2011 PNAS 108(23), pp. 9637-0642.

For such highly elongated and rough surface particles, light scattering intensity varies in time and depends heavily on the orientation of a given particle with respect to the light sheet (different effective cross-sections) and the particle's rotation. In practical terms, images recorded for such particles show characteristic blinking with frequencies of several Hz, while their Brownian translational motion can be separated into two completely different movements, with the Brownian rotation enhancing blinking, a la a disco ball effect (a rotating surface covered with flat mirrors that sheds pulses of light scattered into various directions).

When current instrumentation for sizing nanoparticles by Brownian motion tracking encounters such particles, the instrumentation has severe problems that limit or completely inhibit accurate sizing. The instrumentation observes incomplete nanoparticle tracks that are too short for accurate sizing and are impossible to correct by connecting tracks across multiple video frames when recording videos at standard 30 fps.

Therefore, there exists a need for a system and method that addresses the blinking of a nanoparticles and accounts for nanoparticles that might be elongated, when processing the images, to arrive at a particle size based on Brownian motion.

4.0 SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

The apparatus, systems, and methods described herein elegantly solve the problems presented above. A method allows for the sizing of highly elongated nanoparticles either by their arrangement into a parallel assembly (all particles are directed so their longest dimension axes are parallel; typically this is done by applying an electrical field if the particles have an electrical moment) or by analyzing observed particle size distribution and inferring the maximum, minimum and average sizes from the shape of that distribution. The method allows for the observation of particles that exhibit pulsating light scattering and create certain problems for classical particle tracking analysis (discontinuity of tracks).

The system may include an adjustable light source constructed to direct a beam of electromagnetic radiation at a specimen chamber that allows a portion of the beam to scatter when illuminating particles within the chamber. The scattered portion of the beam is directed to a sensor having a frame rate and a time period between frames. The system may have a processor connected to the sensor and to the light source, and the processor may perform the following steps: activate the light source and obtain images from the sensor; if the images from the sensor show that the particles are blinking, then reduce the frame rate, set the exposure time to be equal at least 60% or more of the time between frames, and reduce the illumination intensity. Then, the processor obtains additional images and processes those images to mitigate blurring. The processor determines the Brownian motion of the particles from the processed images and determines the sizes of the particles based on the motion.

The processor may set a blinking reduction preset and repeat reducing the frame rate and setting the exposure time until the blinking reduction preset has been achieved. The processor may also determine a particle size distribution (PSD) function based on the calculated sizes and, from the PSD, determine whether the particles are elongated.

The sensor may have an image plane, and the system may include electrodes connected to the processor that produce an electric field within the image plane and across in the specimen chamber. The processor may then obtain images from the sensor while actuating the electrodes to produce the electric field and determine the Brownian motion of the particles from the images. The processor may further decompose the motion into a first component that is substantially parallel to the electric field and a second component that is substantially orthogonal to the electric field and, for each component, determine the sizes of the particles.

In a separate embodiment, the system includes an adjustable light source constructed to direct a beam of electromagnetic radiation at a specimen chamber that allows a portion of the beam to scatter when illuminating particles within the chamber. The scattered portion of the beam is directed to a sensor having an image plane. The system may include electrodes connected to the processor that produce an electric field within the image plane and across in the specimen chamber. A processor is connected to the light source, sensor and electrodes, and the processor may obtain images from sensor while actuating the electrodes to produce the electric field and determine the Brownian motion of the particles from the images. The processor may further decompose the motion into a first component that is substantially parallel to the electric field and a second component that is substantially orthogonal to the electric field and, for each component, determine the sizes of the particles.

Before actuating the electrodes to produce the electric field, the processor may first determine if the particles are elongated by: obtaining images from sensor, determining the Brownian motion of the particles from the images, determining the sizes of the particles based on the Brownian motion, calculating a particle size distribution (PSD) function based on the determined sizes, and, from the PSD, determining whether the particles are elongated. If the particles appear to be elongated from the PSD, then the processor may actuate the electrode and obtain images of the particles in the electric field.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

5.0 BRIEF DESCRIPTION OF THE DRAWINGS

The invention can be better understood with reference to the following figures. The components within the figures are not necessarily to scale, emphasis instead being placed on clearly illustrating example aspects of the invention. In the figures reference numerals designate corresponding parts throughout the different views and/or embodiments. It will be understood that certain components and details may not appear in the figures to assist in more clearly describing the invention.

6.0 DETAILED DESCRIPTION

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with the attached figures and is provided for ease of reference, where like reference numerals designate corresponding features throughout the specification and figures:

Image Frame 10
Scattering Nanoparticles 15
Non-scattering Nanoparticles 20
Brownian Translational Movement 25
Grouping 30
Nanoparticle 1, 2, 3 35A, 35B, 35C
Particle Size Distribution (PSD) (Elongated Nanoparticle) 40
Particle Size Distribution (Spherical Nanoparticle) 45
Elongated Nanoparticles in Absence of Electric Field 50
Elongated Nanoparticles in Presence of Electric Field 55
Sensor Image Plane 56
Electric Field 60
Example Brownian Movement Vector 65
First Component of Movement Parallel with Electric Field 70
Second Component of Movement Orthogonal with Electric Field 75
Improved Method to Size Nanoparticles 100
Steps for Improved Method to Size Nanoparticles 105-160
Subroutine for Image Detection, Processing and PSD Plotting 200
Steps for Subroutine for Image Detection, Processing and PSD Plotting 205-220
Subroutine to Reduce Blinking 230
Steps for Subroutine to Reduce Blinking 235-255
Instrument Setup 310
Adjustable Light Source 315
Light Beam 320
Optical Objective 325
Light Sheet 330
Specimen Chamber 335
Scattered Light 340
Focusing Optical Objective 345
Focused Light Beam 350
Sensor (e.g., Camera) 355
Processor 360
Electrodes 365

A complicated situation that is solved in this disclosure involves the tracking of nanoparticles that, due to Brownian rotational movements, exhibit very strong blinking or rapid changes in the intensity of scattered light. This can be also the case of spherical particles that were chipped off from crystalline-like materials, typical of many colloids produced by disintegration of solid rocks in turbid river waters that carry plenty of inorganic materials. Such particles usually have many faces or flat surfaces created by crystalline planes of the originating material. Colloids containing such gem-like particles are nearly impossible to analyze using standard particle tracking methods because rapid changes in the intensity of scattered light (blinking) prevents recording of continuous tracks depicting Brownian motion, as discussed above.

Figure 1:
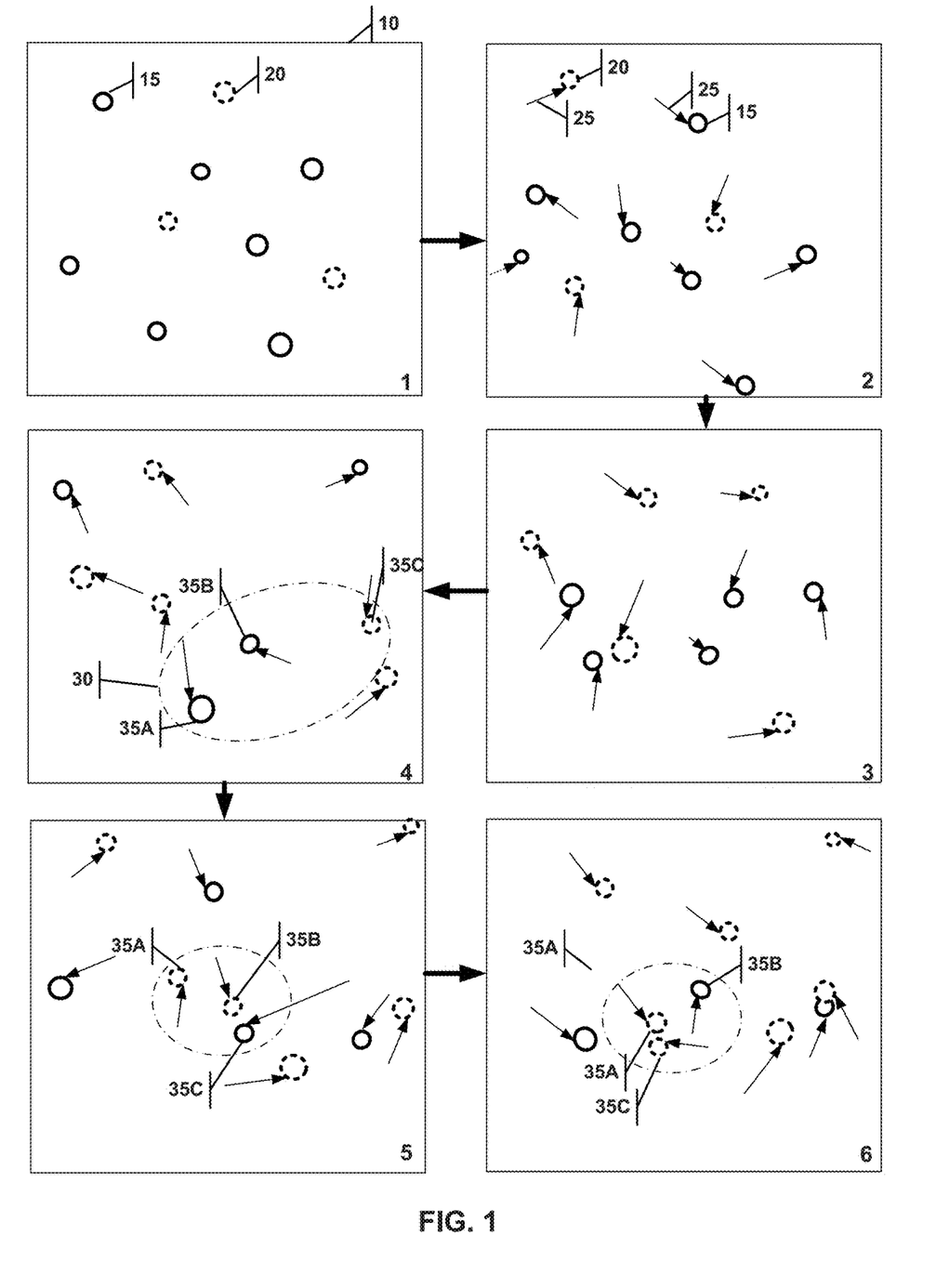
FIG. 1 is a series of image frames taken at a fast rate, showing the blinking of nanoparticles.

FIG. 1 represents six image frames 10 of video taken at 30 frames/second (fps). Nanoparticles are either scattering 15 (solid circle) or non-scattering 20 (dashed circle). So any non-scattering nanoparticle 20 will not be detected by the sensor 355 that is capturing these image frames. Because the nanoparticles 15, 20 experience both translational (shown by arrow 25), and rotational Brownian movement, nanoparticles 15, 20 can scatter in one frame and disappear in the next, only to re-appear later in a completely different position, making tracking of the particles impossible. Without accurate tracking of Brownian movement, the particle size cannot be accurately calculated.

The grouping 30 in frames 4, 5 and 6 of FIG. 1 illustrates the "blinking" and the movement of the three nanoparticles 35A, 35B and 35C. Within this grouping 30, the processor 360 may make the mistake of determining that the nanoparticle 35B (frame 4) moved and is the same nanoparticle 35C (frame 5), when in fact the movement of nanoparticle 35B was completely different than what was determined by the processor 360.

The proposed solution in such cases is to use of an extremely low number of recorded frames per second. Instead of a typical 30 fps, one should use a 10× smaller number of frames per second and, at the same time, apply increased exposure time. As an example, when using 30 fps, one typically employs exposure times of about 15 msec, or about half of the time between frames (in this case 33 msec). With 4 fps or 250 msec frame length, one should use an exposure time of at least 200 msec, which of course necessitates instrumentation that allows for not only changes in camera gain but also the possibility of lowering the power of the illuminating laser to prevent overexposure of imaged particles.

But having a long exposure introduces its own problem. Images on subsequent frames become fuzzy because of Brownian motion during exposure. Proper statistical methods can resolve such fuzziness that is detrimental to accuracy of particle size determination, cf. e.g. X. Michalet and A. J. Berglund 2012 Phys Rev E85, pp. 061916-1-061916-14. Such low fps measurements are possible, and they can give an accurate sizing of observed particles because much longer tracks lasting for many seconds can be recorded and processed automatically by modern processors.

Figure 4A:
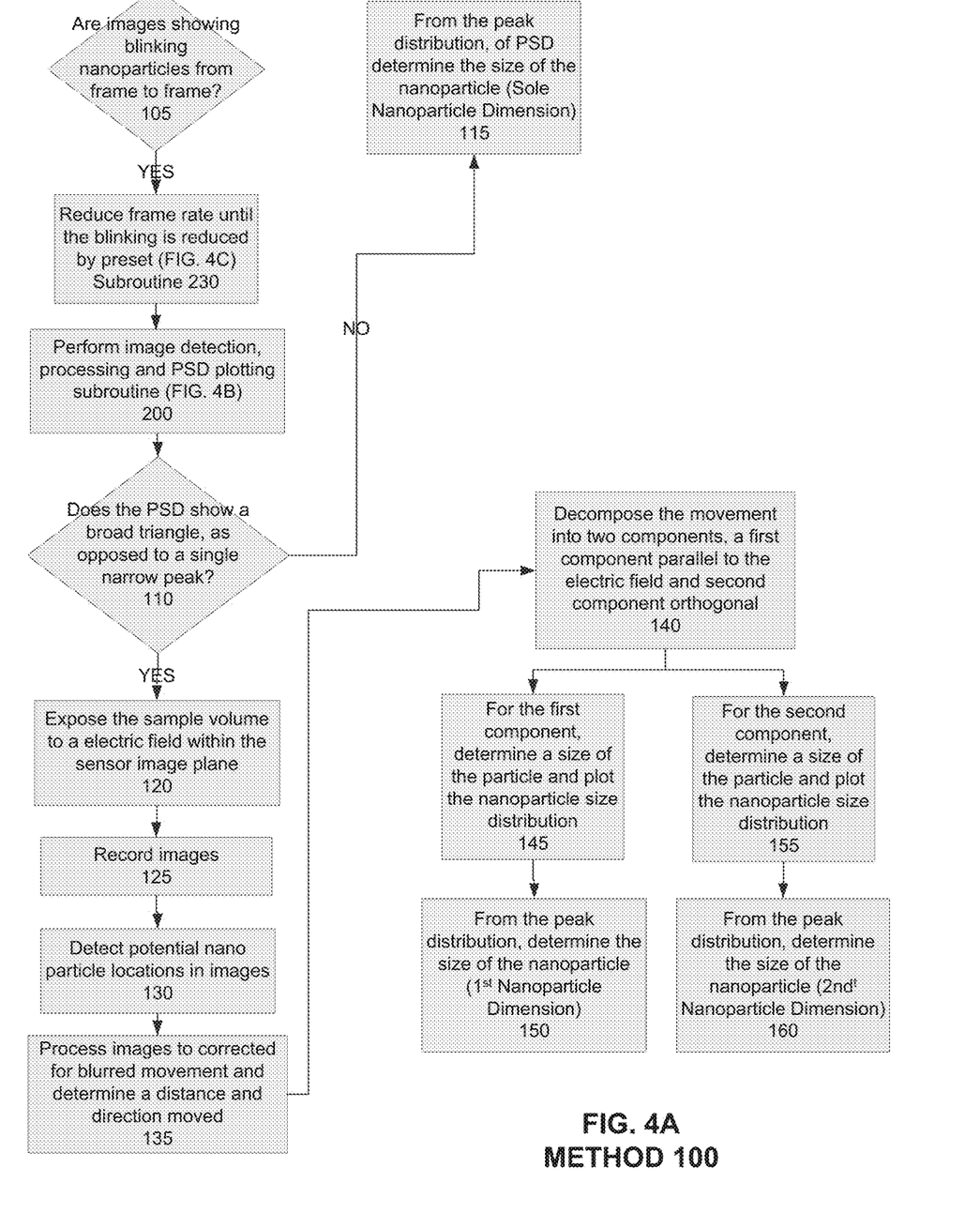
FIG. 4A is an improved method to size particles.
Figure 4B:
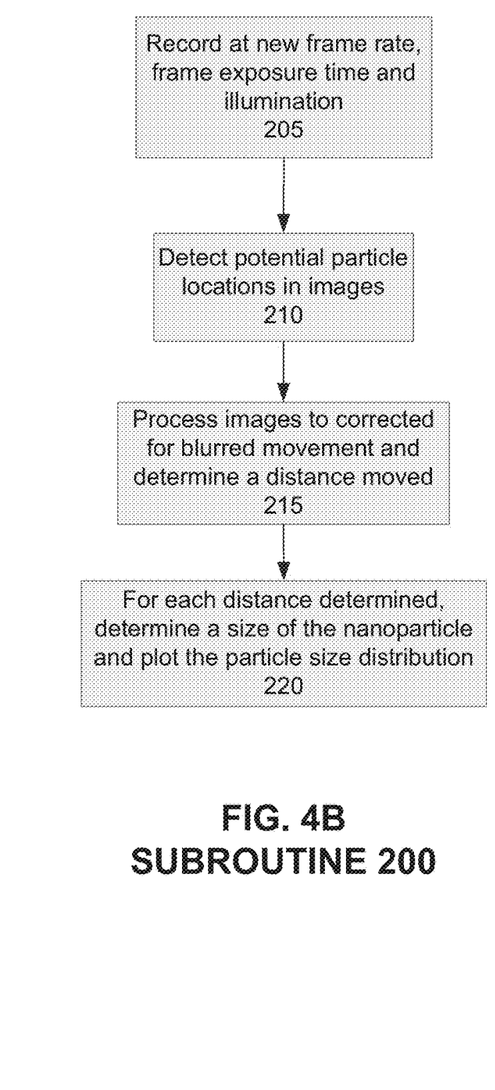
FIG. 4B is a subroutine for image detection, processing and PSD plotting.
Figure 4C:
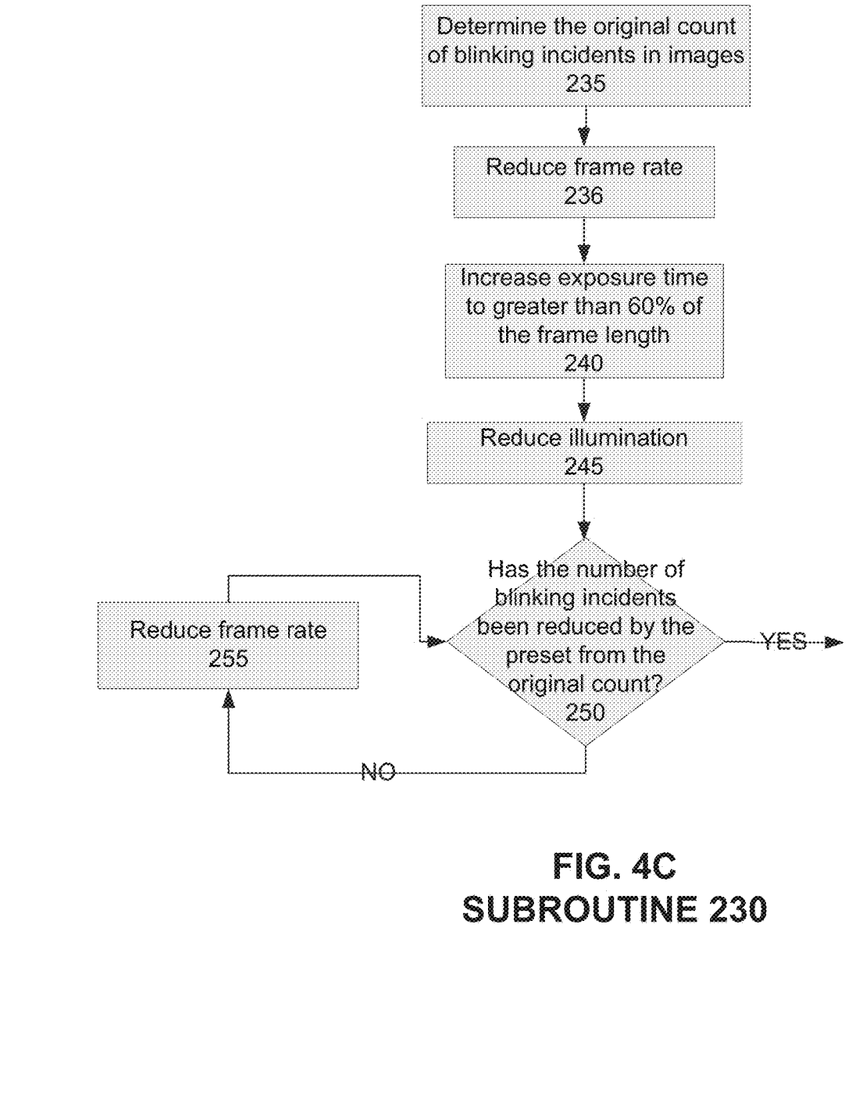
FIG. 4C is a subroutine to reduce blinking.

FIG. 4A discloses a method that mitigates the effects of nanoparticle "blinking". If the nanoparticles are blinking (step 105), then the subroutine 230 is engaged. First, the system determines the original count of blinking incidents in the images (step 235) and then reduces the frame rate and increases the exposure time to be equal at least 60% of the time between frames (step 240). Because the exposure time for each frame is increased, the illumination should be reduced; otherwise, nanoparticles will scatter too much light and drown out adjacent particles, rendering those adjacent particles invisible to the sensors (step 245). The system then checks if the number of blinking incidents has been reduced sufficiently in step 250, and if not, the frame rate is again reduced (step 255). Although not shown, if the frame rate is again reduced, the exposure time will be increased, and the illumination may need to be again reduced. The system continues to check after frame rate reductions until the blinking incidents have been reduced to a preset value. This value may be set to optimize the ability of the processor to de-blur the images to achieve accurate particle tracking.

Instead of engaging in the subroutine 230, the system may just reduce the frame rate to 4 fps with at least a 200 msec exposure for each frame.

After the blinking has been addressed, the system may perform the subroutine 200, which entails recording images at the new frame rate, frame exposure length and illumination (step 205). Then, the system detects the particle locations in step 210 and processes the images to correct for the blurred movement to arrive at an accurate tracking of the distance moved in step 215. From this movement, the particle size can be determined and plotted in step 220.

The remainder of the method shown in FIG. 4A relates to the problems associated with an elongated particle, which will now be discussed. Brownian movements of elongated particles are naturally separated into two components: movements along longer axis are more vigorous, while movements in the direction perpendicular to that axis are more constrained due to viscosity of the diluent. This means that sizes inferred from Brownian movements in each direction will be different. It is expected that movements along the longer axis will represent the small diameter of each particle (movements will be more vigorous), while movements perpendicular to the longer axis will correspond to much larger size or length (movements will be smaller). If Brownian rotation perpendicular to the longer axis of the tracked particles is slow as compared to the observation time (several seconds), one will notice distribution of apparent sizes between the diameter of the rod-like particles and their length. Practically, it means that a very broad distribution of sizes, with the most probable size being the average of two dimensions: the diameter and the length of a particle. In the case of an example of TMVs mentioned in the introduction, this is about 160 nm with a distribution extending from nearly zero up to 300 nm diameters or even more, due to the natural broadening of the distribution (limited number of tracking steps in the tracking process).

Figure 2A:
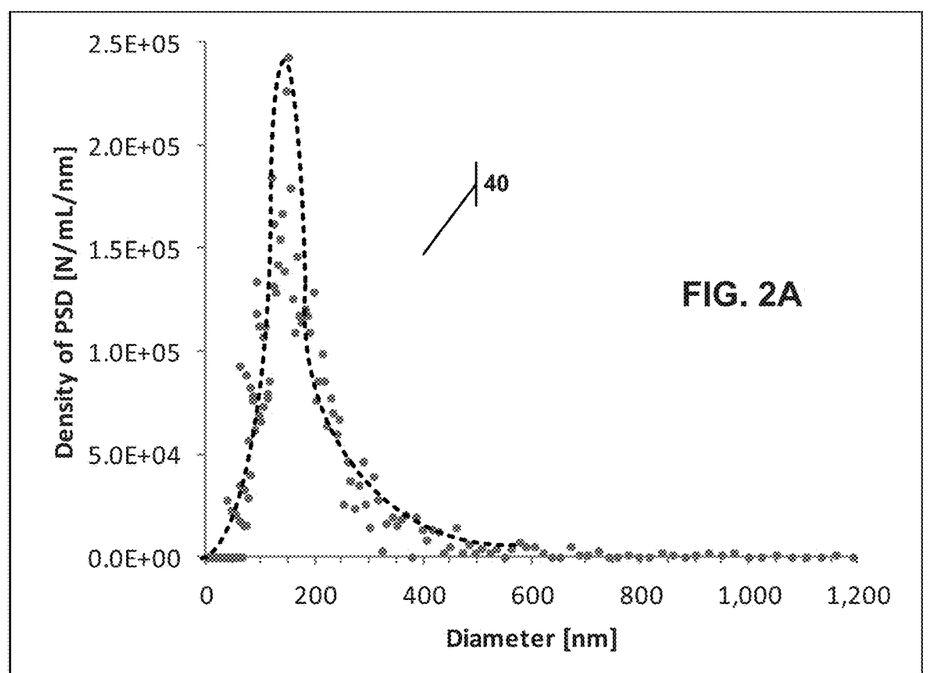
FIG. 2A is the particle size distribution of an elongated nanoparticle colloid.
Figure 2B:
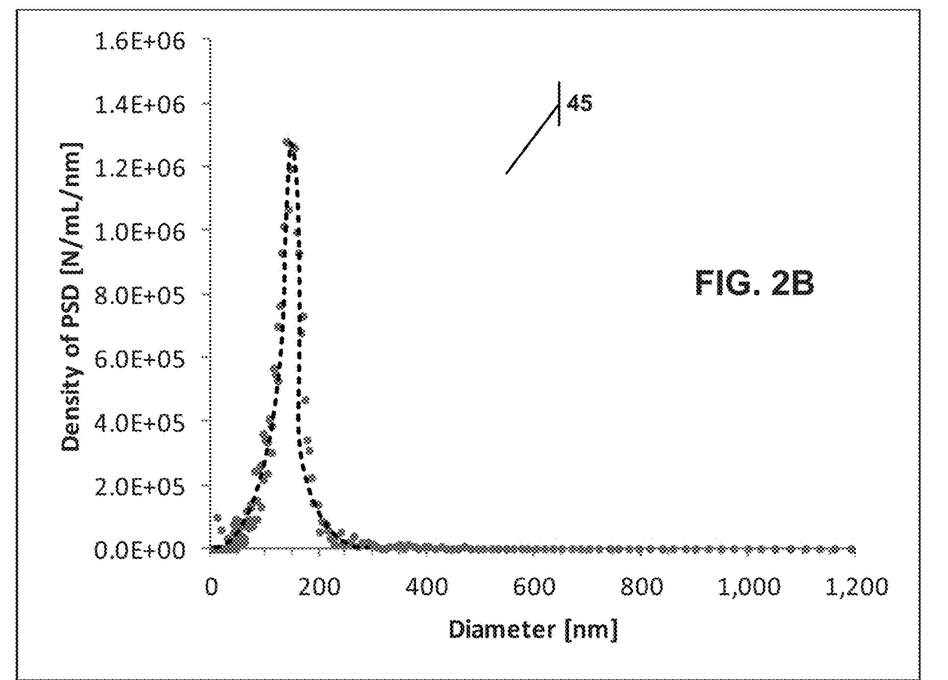
FIG. 2B is the particle size distribution of a spherical nanoparticle colloid.

FIG. 2A presents such a distribution 40 measured experimentally with special recording conditions specific to the method being patented, imposed to mitigate blinking. For comparison, FIG. 2B illustrates the particle size distribution function (PSD) 45 for a spherical nanoparticle. The base of the elongated nanoparticle is much broader than the sharp and narrow base of the spherical nanoparticle. Therefore, by analyzing the PSD, the system can determine that the observed nanoparticles are elongated and can take steps to increase the accuracy of the Brownian tracking, and thus improve the accuracy of the size calculations.

Figure 3A:
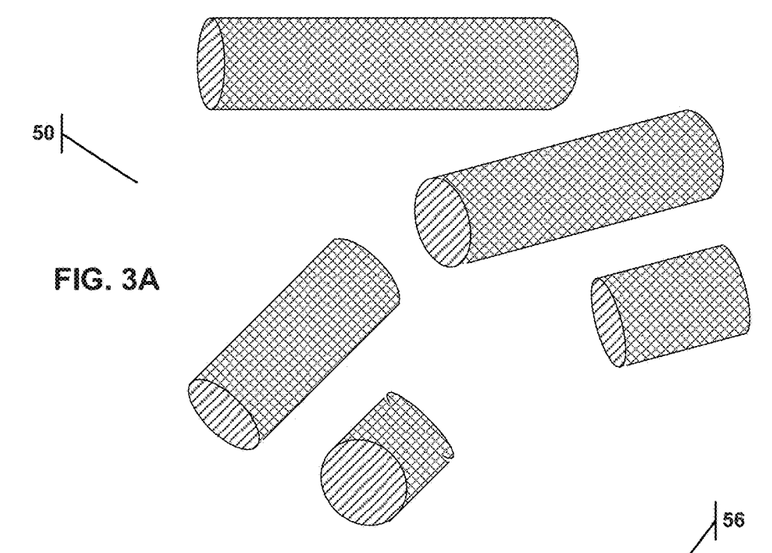
FIG. 3A illustrates several elongated nanoparticle in a solution.
Figure 3B:
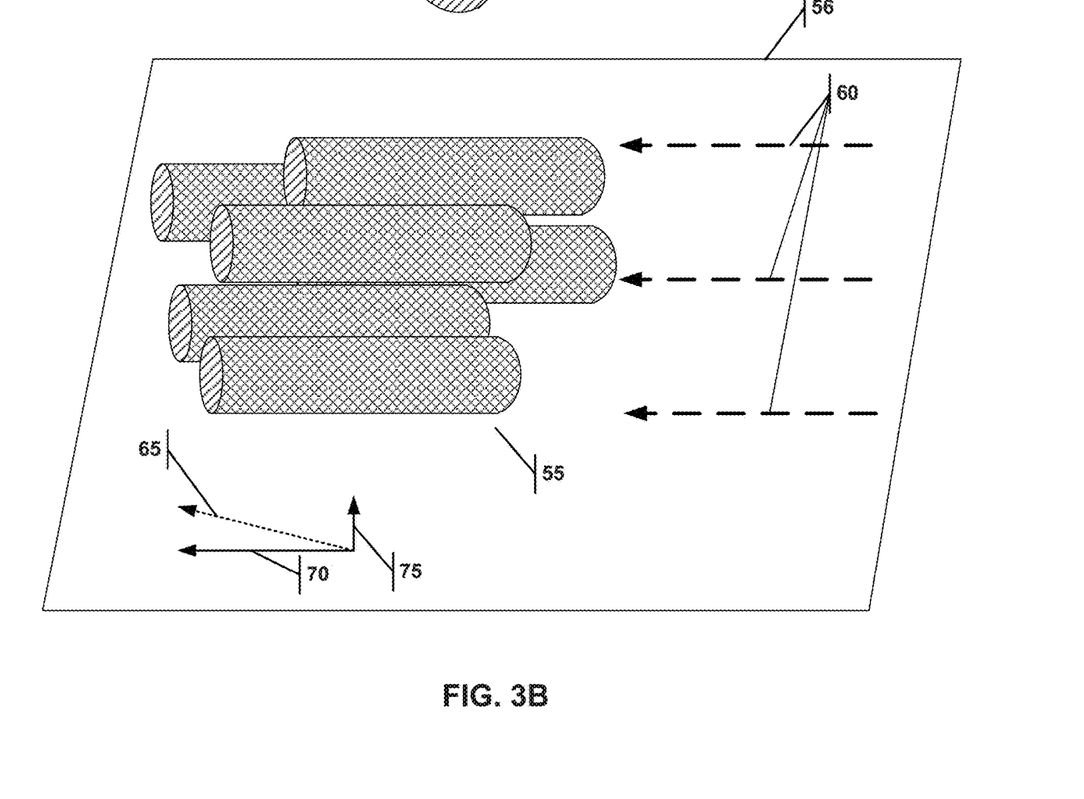
FIG. 3B illustrates several elongated nanoparticles in a solution aligned in an electric field that is parallel to the image plane.

FIG. 3A illustrates several elongated nanoparticles 50 that are randomly suspended in a colloid. When the particles have an electric dipole moment, i.e. they can interact with a static electric field by aligning their axis with the field, such a field can be used to accurately determine the size of the particles in two projections. FIG. 3B illustrates the application of an electric field 60 within the image plane 56 of the sensor 355, which aligns the elongated nanoparticles 55. If the nanoparticles 55 are all aligned, then Brownian motion distances observed as a projection on the surface of a camera's sensor 355 will give two different sizes, depending on the direction of tracking (along 70 or perpendicular 75 to the direction of the field applied). In such cases, to get the dimensions of elongated nanoparticles present in a colloid, one just needs to perform standard Brownian analysis of mean square distance but do that separately in two perpendicular components 70, 75. Specifically, if the nanoparticles Brownian motion is represented by vector 65, then that can be decomposed into a first component parallel with the electric field 70 and a second component orthogonal to the electric field 75. For simplicity, the electric field 60 can be constructed to align the nanoparticles 55 along the rows or the columns of sensor's pixels.

Returning to FIG. 4A, the system may determine from the PSD 45 whether there is a broad based-triangle (step 110—"broad-based triangle" denotes a shape of the PSD 45 that resembles a triangle with a horizontal side extending from a very small size of about 10 nm up to the maximum expected length of elongated particles, e.g. 300 nm in case of MTVs, with the understanding that the tail of the PSD 45 can be extended to even larger values due to aggregates of particles and the small number of impurities always present in colloids), and, if so, expose the sample volume to an electric field 60 within the sensor image plane 56 (step 120). The system records the images, detects the locations of the nanoparticles in the images and de-blurs the images to arrive at a distance and directions moved in steps 125-130. Then in step 140 the movement is decomposed into a first and second component (70, 75). Based on the first component 70, which is parallel to the electric field 60, the size of the nanoparticle 55 is determined and plotted (step 145), from which the size of the nanoparticle 55 is determined, representing the first nanoparticle dimension (step 150). The same is done based on the second component 75, which is orthogonal to the first component 70, as shown in steps 155 and 160.

Figure 5:
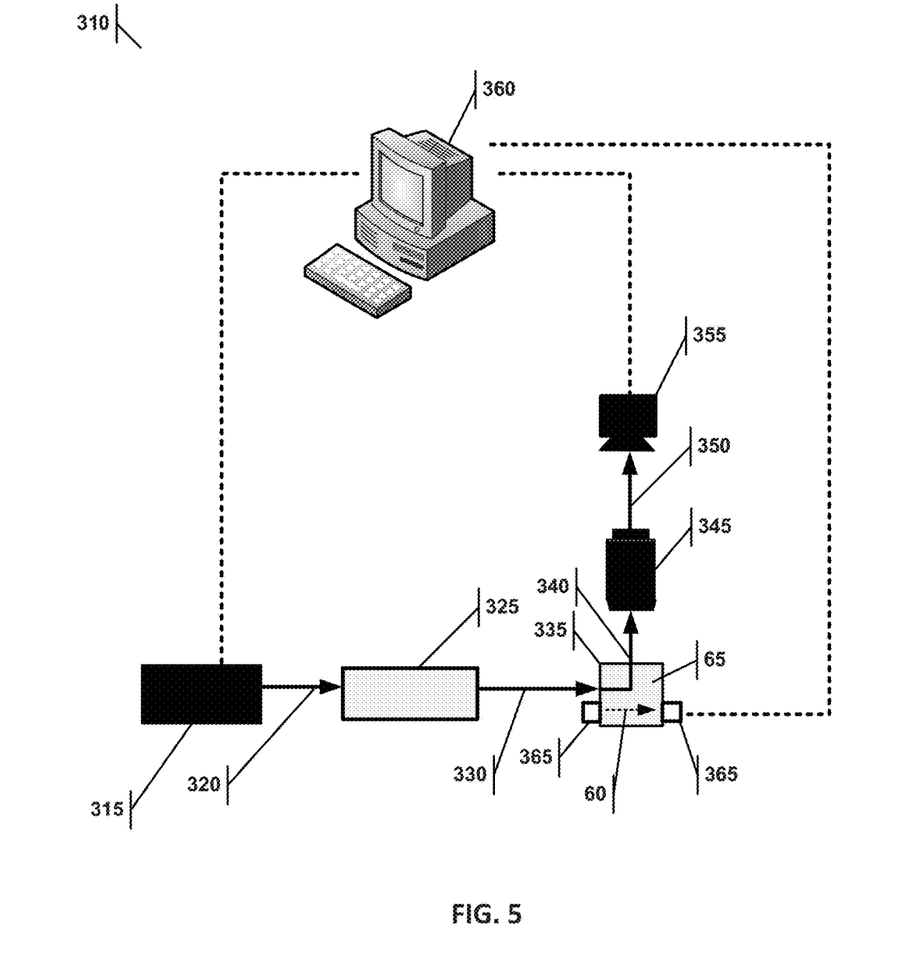
FIG. 5 is a schematic of an instrument setup.

FIG. 5 illustrates a system using the methods and devices disclosed herein. The system includes an adjustable light source 315 that produces a light beam 320 that passes through a cylindrical lens and an optical objective 325 that form a light sheet 330, which is directed at the specimen chamber 335. The chamber 335 contains the nanoparticles in a colloid made out of a diluent. Electrodes 365, when actuated, cause an electric field 60 across the specimen chamber 335.

The nanoparticles in the chamber 335 scatter light 340 that is directed through a focusing optical objective 345, which may also include magnifying optical objectives—i.e., a microscope, producing a focused light beam 350 onto a sensor (e.g., camera) 355. A processor 360 may be connected to the sensor 355, the light source 315 and the electrodes 365 to control them. The setup 310 enables the illumination of any liquid with a precisely-formed, narrow light sheet 330 and the observation of scattered light 340 from the nanoparticles, usually at a 90-degree angle relative to the light sheet plane. In other words, the direction of observation is perpendicular to the direction of the plane of illumination. The processor 360 may be configured to perform the methods disclosed herein.

Although exemplary embodiments and applications of the invention have been described herein, including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible, as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A method for determining the size of particles for use in a system that comprises an adjustable light source constructed to direct a beam of electromagnetic radiation at a specimen chamber that allows a portion of the beam to scatter when illuminating the particles within the chamber, wherein the scattered portion is directed to a sensor, the sensor having a frame rate with a time period between frames, the method comprising:
   A. activating the light source and obtaining images from sensor;
   B. if the images from the sensor show that particles are blinking;
      i. reducing the frame rate;
      ii. setting an exposure time to at least 60% of the time between frames;
      iii. reducing illumination;
   C. obtaining images from the sensor based on the new settings of step (B);
   D. processing images to mitigate blurring;
   E. determining the Brownian motion of the particles from the processed images;
   F. determining the sizes of the particles based on the Brownian motion.

2. The method of claim 1, further comprising setting a blinking reduction preset, and repeating steps (B)(i) and (ii) until the blinking reduction preset has been achieved.

3. The method of claim 1, further comprising:
   G. determining a particle size distribution (PSD) function based on the determined sizes;
   H. from the PSD, determining whether the particles are elongated.

4. The method of claim 3, wherein the system sensor has an image plane, and the system comprises electrodes constructed to produce an electric field with in the image plane and across in the specimen chamber, the method further comprising:
   I. obtaining images from the sensor while actuating the electrodes to produce the electric field;
   J. determining the Brownian motion of the particles from the images of step (I);
   K. decomposing the motion into a first component that is substantially parallel to the electric field and a second component that is substantially orthogonal to the electric field;
   L. for each component, determining the sizes of the particles.

5. A system for determining the particle size distribution of a colloid, the system comprising:
   an adjustable light source constructed to direct a beam of electromagnetic radiation at a specimen chamber, the chamber constructed to allow a portion of the beam to scatter when illuminating particles within the chamber;
   a sensor positioned to detect the scatter of the beam, the sensor having a frame rate with a time period between frames;
   a processor connected to the light source; and the sensor, the processor configured to perform the following steps:
      A. activating the light source and obtaining images from the sensor;
      B. if the images from the sensor show that particles are blinking;
         i. reducing the frame rate;
         ii. setting an exposure time to at least 60% of the time between frames;
         iii. reducing illumination;
      C. obtaining images from the sensor based on the new settings of step (B);
      D. processing images to mitigate blurring;
      E. determining the Brownian motion of the particles from the processed images;
      F. determining the sizes of the particles based on the Brownian motion.

6. The system of claim 5, wherein the processor performs the following step: setting a blinking reduction preset, and repeating steps (B)(i) and (ii) until the blinking reduction preset has been achieved.

7. The system of claim 5, wherein the processor performs the following steps:
   G. determining a particle size distribution (PSD) function based on the determined sizes;
   H. from the PSD, determining whether the particles are elongated.

8. The system of claim 7, wherein the system sensor has an image plane, and the system comprises electrodes connected to the processor and constructed to produce an electric field within the image plane and across the specimen chamber, wherein the processor performs the following steps:
   I. obtaining images from the sensor while actuating the electrodes to produce the electric field;
   J. determining the Brownian motion of the particles from the images of step (I);
   K. decomposing the motion into a first component that is substantially parallel to the electric field and a second component that is substantially orthogonal to the electric field;
   L. for each component, determining the sizes of the particles.

9. A method for determining the size of particles for use in a system that comprises a light source constructed to direct a beam of electromagnetic radiation at a specimen chamber that allows a portion of the beam to scatter when illuminating particles within the chamber, wherein the scattered portion is directed to a sensor the sensor having an image plane, wherein the system further comprises electrodes constructed to produce an electric field within the image plane and across the specimen chamber, the method comprising:
   A. activating the light source;
   B. obtaining images from the sensor while actuating the electrodes to produce the electric field;
   C. determining the Brownian motion of the particles from the images of step (B);
   D. decomposing the motion into a first component that is substantially parallel to the electric field and a second component that is substantially orthogonal to the electric field;
   E. for each component, determining the sizes of the particles.

10. The method of claim 9, further comprising:
   prior to step (B):
      (1) obtaining images from sensor;
      (2) determining the Brownian motion of the particles from the images;
      (3) determining the sizes of the particles based on the Brownian motion;

(4) determining a particle size distribution (PSD) function based on the determined sizes;
(5) from the PSD determining whether the particles are elongated;
(6) if the particles are elongated, continuing to steps (B)-(E).

11. A system for determining the particle size distribution of a colloid, the system comprising:
- A light source constructed to direct a beam of electromagnetic radiation at a specimen chamber, the chamber constructed to allow a portion of the beam to scatter when illuminating particles within the chamber;
- a sensor positioned to detect the scatter of the beam, the sensor having an image plane;
- electrodes constructed to produce an electric field within the image plane and across the specimen chamber;
- a processor connected to the light source, sensor and electrodes, the processor configured to perform the following steps:
   A. activating the light source;
   B. obtaining images from sensor while actuating the electrodes to produce the electric field;
   C. determining the Brownian motion of the particles from the images of step (B);
   D. decomposing the motion into a first component that is substantially parallel to the electric field and a second component that is substantially orthogonal to the electric field;
   E. for each component, determining the sizes of the particles.

12. The system of claim 11, wherein the processor performs the following steps before step (B):
(1) obtaining images from the sensor;
(2) determining the Brownian motion of the particles from the images;
(3) determining the sizes of the particles based on the Brownian motion;
(4) determining a particle size distribution (PSD) function based on the determined sizes;
(5) from the PSD, determining whether the particles are elongated;
(6) if the particles are elongated, continuing to steps (B)-(E).

* * * * *